US010047172B2

(12) United States Patent
Boiteau

(10) Patent No.: US 10,047,172 B2
(45) Date of Patent: Aug. 14, 2018

(54) SINGLE STEP FUNCTIONALIZATION AND CROSS-LINKING OF HYALURONIC ACID

(71) Applicant: GALDERMA S.A., Cham (CH)

(72) Inventor: Jean-Guy Boiteau, Valbonne (FR)

(73) Assignee: GALDERMA S.A., Cham (CH)

( * ) Notice: Subject to any disclaimer, the term of this patent is extended or adjusted under 35 U.S.C. 154(b) by 36 days.

(21) Appl. No.: 15/024,647

(22) PCT Filed: Sep. 30, 2014

(86) PCT No.: PCT/EP2014/070943
§ 371 (c)(1),
(2) Date: Mar. 24, 2016

(87) PCT Pub. No.: WO2015/044455
PCT Pub. Date: Apr. 2, 2015

(65) Prior Publication Data
US 2016/0237177 A1 Aug. 18, 2016

(30) Foreign Application Priority Data
Sep. 30, 2013 (EP) .................. 13186638

(51) Int. Cl.
C08B 37/00 (2006.01)
A61K 8/73 (2006.01)
C08B 37/08 (2006.01)
A61L 27/20 (2006.01)
A61L 27/52 (2006.01)
A61L 27/54 (2006.01)
A61Q 19/00 (2006.01)
A61K 49/00 (2006.01)
A61L 27/50 (2006.01)

(52) U.S. Cl.
CPC .......... C08B 37/0072 (2013.01); A61K 8/735 (2013.01); A61K 49/0054 (2013.01); A61L 27/20 (2013.01); A61L 27/50 (2013.01); A61L 27/52 (2013.01); A61L 27/54 (2013.01); A61Q 19/00 (2013.01); A61K 2800/91 (2013.01); A61L 2300/442 (2013.01); A61L 2400/06 (2013.01)

(58) Field of Classification Search
CPC .................................. C08B 37/0072
USPC ....................... 536/53; 514/53, 62
See application file for complete search history.

(56) References Cited

U.S. PATENT DOCUMENTS 4,886,787 A * 12/1989 de Belder ............. A61L 31/042
514/54
5,827,937 A 10/1998 Agerup
2009/0149419 A1 6/2009 Amit et al.
2010/0028437 A1 2/2010 Lebreton
2010/0028438 A1 2/2010 Lebreton
2012/0172328 A1 7/2012 Lebreton
2013/0041038 A1 2/2013 Lebreton
2013/0041039 A1 2/2013 Lebreton
2013/0031011 A1 5/2013 Lebreton
2013/0044970 A1 9/2013 Lebreton
2014/0005141 A1 1/2014 Amit et al.
2014/0213546 A1 7/2014 Lebreton
2014/0213547 A1 7/2014 Lebreton
2015/0231268 A1* 8/2015 Nakai ................ A61K 47/4823
514/20.5

FOREIGN PATENT DOCUMENTS

WO WO 2007/102149 A2 9/2007
WO WO 2008/031525 A1 3/2008

OTHER PUBLICATIONS

International Search Report (PCT/ISA/210) dated Feb. 17, 2015, by the European Office as the International Searching Authority for International Application No. PCT/EP2014/070943.
Written Opinion (PCT/ISA/237) dated Feb. 17, 2015, by the European Patent Office as the International Searching Authority for International Application No. PCT/EP2014/070943.
European Search Report dated Dec. 4, 2013 for Application No. 13186638.6.
Glenn D. Prestwich et al., "Controlled Chemical Modification of Hyaluronic Acid: Synthesis, Applications, and Biodegradation of Hydrazide Derivatives", Journal of Controlled Release, vol. 53, pp. 93-103, 1998.
Tara Pouyani et al., "Functionalized Derivatives of Hyaluronic Acid Oligosaccharides: Drug Carriers and Novel Biomaterials", Bioconjugate Chemistry, 1994, vol. 5; pp. 339-347.
Paul Bulpitt et al., "New Strategy for Chemical Modification of Hyaluronic Acid: Preparation of Functionalized Derivatives and Their Use in the Formation of Novel Biocompatible Hydrogels", J. Biomed. Mater. Res., Sep. 2, 1998. vol. 47, No. 2, pp. 152-169.
Junbin Shi et al., "Cell-Compatible Hydrogels Based on a Multifunctional Crosslinker With Tunable Siffness for Tissue Engineering", Journal of Materials Chemistry, 2012, vol. 22, pp. 23952-23962.
Tao Chen et al., "Modification of Liposomes WIT Proteins by Dansyl-Labeled Heterobifunctional Crosslinker", Journal of Biomaterial Applications, Jul. 2011, vol. 26, pp. 117-125.

* cited by examiner

Primary Examiner — Shaojia A Jiang
Assistant Examiner — Everett White
(74) Attorney, Agent, or Firm — Buchanan Ingersoll & Rooney P.C.

(57) ABSTRACT

A process for manufacturing a cross-linked hyaluronic acid (HA) containing a functionalizing group including the step of reacting HA with a mixture of: (i) a first cross-linking agent selected from the group of bifunctional epoxides and polyfunctional epoxides, and (ii) a functionalized agent of a functionalizing group coupled via a 1,2,3-triazole linkage to a second cross-linking agent selected from the group of bifunctional epoxides and polyfunctional epoxides, to obtain a cross-linked HA containing the functionalizing group. The process provides a cross-linked hyaluronic acid (HA) containing a functionalizing group. The process utilizes a functionalized agent of a functionalizing group coupled via a 1,2,3-triazole linkage to a cross-linking agent.

6 Claims, 1 Drawing Sheet

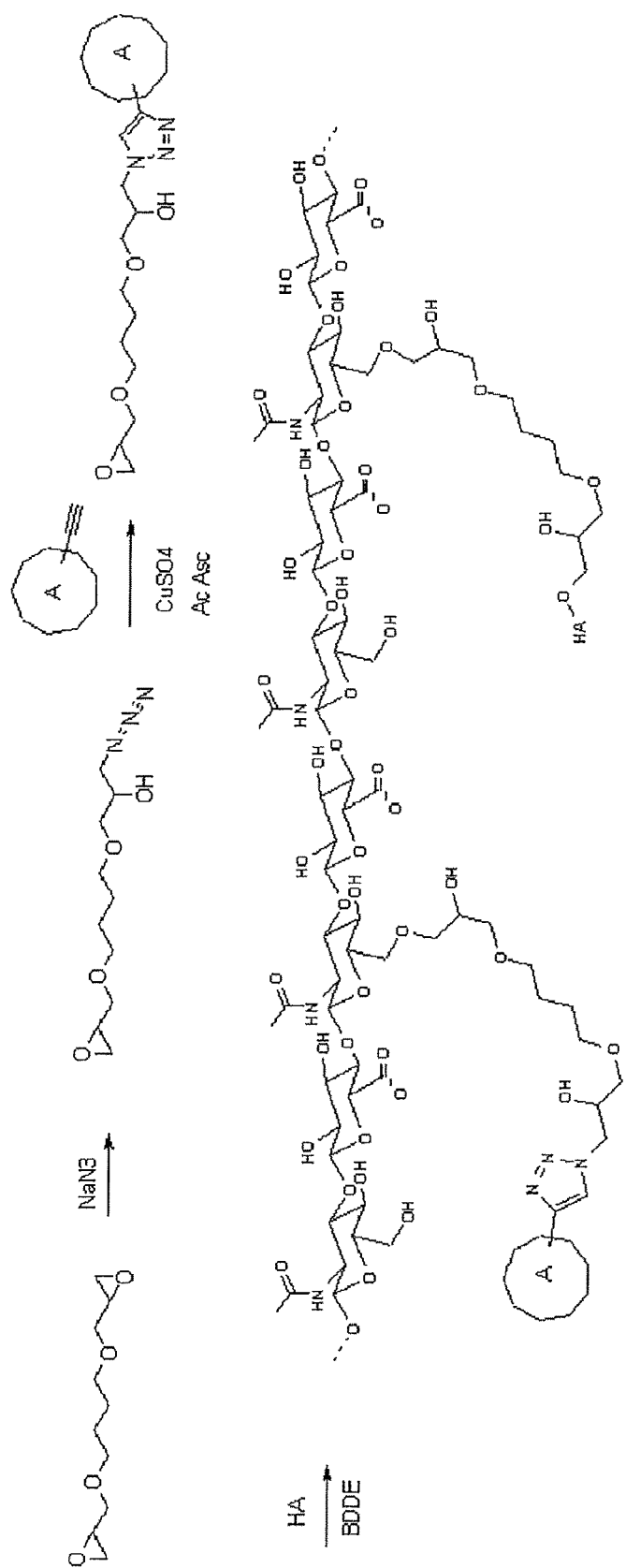

SINGLE STEP FUNCTIONALIZATION AND CROSS-LINKING OF HYALURONIC ACID

FIELD OF THE INVENTION

The present invention relates to a cross-linked hyaluronic acid containing a functionalizing group, to a process for manufacturing the same, and use of the same in the cosmetic and medical fields.

BACKGROUND OF THE INVENTION

Hyaluronic acid (HA) is a polysaccharide composed of a disaccharide motif comprising D-glucuronic acid and N-acetyl-D-glucosamine linked by alternating β(1,4)- and β(1,3)-glycosidic bonds.

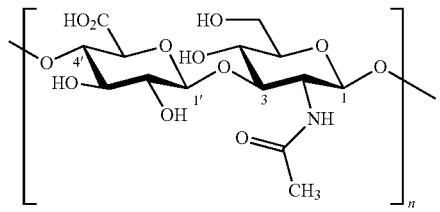

Glucuronic Acid N-Acetyl-D-glucosamine

HA can be cross-linked by various cross-linking agents, e.g. bi- or polyfunctional epoxides, formaldehyde, gluteraldehyde and divinyl sulfone. Cross-linked HA gels using the bifunctional epoxide 1,4-butanediol diglycidyl ether (BDDE) are commercially available e.g. under the trademarks Restylane or Juvederm.

Numerous methods for chemical modification have been employed in order to functionalize and thereby impart new or modified properties to the cross-linked HA.

The chemical modifications can be realized via available —COOH groups of the HA by preactivation with carbodiimides, such as 1-ethyl-3-[3-(dimethylamino)-propyl]-carbodiimide (EDC). N-hydroxysuccinimide (NHS) or 1-hydroxybenzotriazole (HOBt) may also be used together with the EDC to facilitate the coupling reaction. The coupling reactions may also be achieved by the use of 1,1-carbonyldiimidazole (CDI), see e.g. WO 00/01733. These reactions can be performed in water or by adding a co-solvent, such as DMSO.

T. Pouyani & G. D. Prestwich, Bioconjugate Chemistry 5: 339-347 (1994) discloses carbodiimide-mediated coupling of hydrazides to very short oligosaccharide fragments of HA. The oligosaccharide is activated in a first step by the coupling of a hydrazide, followed by a second step where a desired substance can be reacted with the hydrazide-activated oligo-saccharide and become incorporated on the oligosaccharide. Alternatively, the hydrazide-activated oligosaccharide can in a second step be reacted with a cross-linker to obtain a cross-linked oligosaccharide.

G. D. Prestwich et al., J. Control. Release 53 (1-3): 93-103 (1998) discloses a complicated multi-step process involving carbodiimide-mediated coupling of hydrazides to HA. The HA is activated in a first step by the coupling of a hydrazide, followed by a second step where a desired substance can be reacted with the hydrazide-activated HA, and a third step of reacting this functionalized HA with an already cross-linked HA.

P. Bulpitt et al., J. Biomed. Mater. Res. 47 (2):152-169 also discloses a multi-step process involving carbodiimide-mediated coupling of hydrazides to HA. The HA is activated in a first step by the coupling of a hydrazide, followed by a second step where a desired substance can be reacted with the hydrazide-activated HA, and a third step of cross-linking this functionalized HA with a cross-linker.

WO 2007/102149 A2 also discloses a multi-step process involving carbodiimide-mediated coupling of hydrazides to HA. The HA is activated in a first step by the coupling of a hydrazide, followed by a second step of cross-linking this hydrazide-activated HA with a cross-linker. Additional components may be coupled to the hydrazide-functionalized HA in a separate step, before or after the cross-linking step.

The chemical modifications can also be realized via available —OH groups of the HA by reaction with acyl chlorides in a solvent, such as DMSO, or using anhydrides in water (pH=9), see e.g. WO 2007/033677. The —OH groups of the HA can also be functionalized with amines using cyanogen bromide as an activation reagent.

The reported methods for functionalizing cross-linked HA involve functionalizing of the HA prior to cross-linking, followed by cross-linking of the functionalized HA. This method is disadvantageous because it requires modification and purification of a large molecular weight polysaccharide, and because the cross-linking step may result in uncontrolled reaction of the cross-linking agent with the grafted molecule.

Alternatively, the reported methods for functionalizing cross-linked HA involve cross-linking the HA prior to the functionalization, followed by functionalizing of the cross-linked HA. This method is disadvantageous because of difficulties in purifying the resulting gel from by-products formed during the reaction. Moreover, the resulting gel is not homogeneous because the functionalization tends to be formed on the surface of particles.

WO 2008/031525 teaches cross-linking of HA by click chemistry. The cross-linking process involves several time-consuming steps of modifying the sensitive HA with a multiplicity of reagents to allow for the cross-linking reaction.

SUMMARY OF THE INVENTION

It is an object of the present invention to provide a process for manufacturing a cross-linked HA containing a functionalizing group, which overcomes one or more of the drawbacks of the prior art methods.

It is a further object of the present invention to provide a functionalized, cross-linked HA resulting from the new manufacturing process.

For these and other objects that will be evident from the detailed description and the accompanying examples, the present invention provides according to a first aspect a process for manufacturing a cross-linked HA containing a functionalizing group, comprising the step of reacting HA in a single step with a mixture of:
(i) a first cross-linking agent selected from the group consisting of bifunctional epoxides and polyfunctional epoxides, and
(ii) a functionalized agent, consisting of a functionalizing group coupled via a 1,2,3-triazole linkage to a second cross-linking agent selected from the group consisting of bifunctional epoxides and polyfunctional epoxides, to obtain a cross-linked HA containing the functionalizing group.

The present invention is generally based on the insight that a manufacturing process involving simultaneous cross-linking and functionalization of HA in a single step overcomes one or more of the drawbacks of the prior art methods for producing a cross-linked HA containing a functionalizing group and provides a functionalized, cross-linked HA with attractive properties. The implementation of this approach has now successfully been achieved by allowing the HA to react with a mixture of a cross-linking agent and a functionalized agent in a single step, but without introducing any unconventional residues from the cross-linking reaction in the cross-links linking the HA chains. The process according to the invention advantageously allows for simultaneous cross-linking and functionalization of HA without any prior chemical modifications of the HA, which may negatively affect the sensitive HA molecule.

In a preferred manufacturing process according to the invention, the first and second cross-linking agents are independently selected from the group consisting of bifunctional epoxides and polyfunctional epoxides. The single reacting step is performed at a basic pH to provide ether cross-links both between the HA and the first cross-linking agent, and between the HA and the functionalized agent. It is preferred that the first and second cross-linking agents are independently selected from the group consisting of bifunctional epoxides, preferably diglycidyl ethers. It is particularly preferred that the first and second cross-linking agents are both butanediol diglycidyl ether (BDDE).

In one preferred manufacturing process according to the invention, the functionalizing group is an imaging agent. The imaging agent is preferably a fluorescent agent, such as fluorescein.

According to another aspect, the present invention provides a cross-linked hyaluronic acid containing a functionalizing group coupled to the hyaluronic acid via a 1,2,3-triazole linkage and an ether linkage, wherein the hyaluronic acid is cross-linked using the same type of ether linkage.

In one preferred product according to the invention, the functionalizing group is an imaging agent. The imaging agent is preferably a fluorescent agent, such as fluorescein.

In a preferred product according to the invention, the cross-linked hyaluronic acid containing a functionalizing group is obtainable, or obtained, by the manufacturing process according to the invention.

According to further aspects, the present invention provides a functionalized agent, and use of the same for the manufacture of a cross-linked hyaluronic acid containing a functionalizing group. The functionalized agent is consisting of a functionalizing group coupled via a 1,2,3-triazole linkage to a cross-linking agent selected from bifunctional epoxides and polyfunctional epoxides.

In a preferred functionalized agent according to the invention, the cross-linking agent is selected from bifunctional epoxides, preferably diglycidyl ethers. It is particularly preferred that the cross-linking agent is butanediol diglycidyl ether (BDDE).

In one preferred functionalized agent according to the invention, the functionalizing group is an imaging agent. The imaging agent is preferably a fluorescent agent, such as fluorescein.

According to another aspect, the present invention provides the use of a functionalized agent according to the invention and a cross-linking agent selected from the group consisting of bifunctional epoxides and polyfunctional epoxides for the simultaneous functionalizing and cross-linking of hyaluronic acid. The present invention also provides the use of a functionalized agent according to the invention for the manufacture of a cross-linked hyaluronic acid containing a functionalizing group.

BRIEF DESCRIPTION OF THE DRAWINGS

FIG. 1 schematically illustrates the manufacturing process according to the invention, using BDDE as the cross-linking reagent. Functionalization and cross-linking of HA are performed simultaneously, i.e. in a single step reaction.

DETAILED DESCRIPTION OF THE INVENTION

The present invention provides according to a first aspect a manufacturing process involving an entirely new concept: simultaneous cross-linking and functionalization of HA. This is achieved by allowing the cross-linking of HA to occur in the presence of a mixture of a cross-linking agent and a functionalized agent. Thereby, functionalization and cross-linking of HA are performed simultaneously, i.e. in a single step reaction. The functionalization of the cross-linking agent to obtain a functionalized agent is achieved prior to the reaction thereof with HA, while no prior modification of the HA is required. This is advantageous since the HA may be degraded during any work-up steps prior to the cross-linking process.

Specifically, it has been found that bi- or polyfunctional epoxides are useful as cross-linking agents to be used for the functionalization. The usefulness of these epoxides in the provision of a functionalized agent is surprising considering their high reactivity and the risk that the epoxide can react on another part of the same molecule. A skilled person would not have selected epoxides as a basis for the functionalized agent, since they are far more difficult to functionalize than e.g. an hydrazide. It is also surprising that functionalized agents based on these epoxides are useful together with non-functionalized epoxide cross-linking agents in a simultaneous functionalizing and cross-linking reaction of HA.

As set out for the bifunctional epoxide BDDE in FIG. 1, one of the epoxide groups is activated to produce a modified cross-linking agent carrying an azido group. It follows that one of the epoxide functions is modified with an azido function. The functional group of interest, termed A in FIG. 1, is activated by reaction of a suitable reactive group on the functionalizing group of interest to produce a modified functionalizing group carrying an alkyne group. The azide (modified epoxide cross-linking agent) and the alkyne (modified functionalizing group) are allowed to react and form a 1,2,3-triazole linking the modified epoxide agent to the functionalizing group A, as shown for BDDE in FIG. 1. This reaction typically occurs in the presence of a catalyst, such as Cu. It is understood that this reaction removes at least one binding functionality from the bifunctional or polyfunctional epoxide. It follows that when the functionalized agent is prepared from a bifunctional epoxide, the resulting functionalized agent is not a cross-linking agent in the sense that it cannot provide cross-links between HA chains. When the functionalized agent is prepared from a multifunctional epoxide, the resulting functionalized agent may be a cross-linking agent in the sense that it can provide cross-links between HA chains, using the remaining binding functions.

The resulting compound, a functionalized agent, can then be allowed to react in a single step with HA in mixture with a non-functionalized cross-linking agent in varying relative amounts. In the preferred case that BDDE is selected as cross-linking agent both for the HA/functionalizing group and the HA/HA cross-links, this mixture accordingly contains a traditional, bifunctional BDDE together with a monofunctional BDDE, which is modified to include a functionalizing group (A-BDDE in FIG. 1). In a preferred embodiment, the ratio between the bifunctional cross-linking agent and the monofunctional functionalized agent in the mixture is in the range of from 1:100, such as from 1:10, such as from 1:1, to 100:1, such as to 10:1, such as to 1:1.

The cross-linking agents are preferably individually selected from the group consisting of bifunctional epoxides, such as butanediol diglycidyl ether (BDDE), 1,2,3,4,-diepoxybutane and 1,2,7,8-diepoxyoctane. The cross-linking agents are preferably individually selected from the group consisting of diglycidyl ethers, particularly BDDE. The first and second cross-linking agents may be different or identical, and they are preferably identical. Identical cross-linking agents are more convenient to use as the cross-linking of HA and the functionalization of the cross-linked HA surprisingly proceeds with similar speed under the reacting conditions.

The functionalizing group may be any chemical molecule that it is desirable to incorporate by covalent bonds, or graft, into a cross-linked HA gel to provide a new function to the material. The skilled person is familiar with various types of functionalizing groups, which may have a biological, medicinal or technical activity or relevance. Considering the well-known coupling chemistry of bifunctional epoxides and polyfunctional epoxides, the skilled person immediately realizes in the light of the present disclosure that, for practical purposes, virtually any functionalizing group can be presented in the functionalized agent and incorporated into the final cross-linked HA (see e.g. WO 87/07898).

The functionalizing group does not in turn provide a further covalent binding function for permanently further modifying the cross-linked HA, but rather constitutes the final desired modification of the cross-linked HA. It is however understood that the functionalizing group may carry out its function, e.g. imaging, through non-covalent bonds or at least non-permanent bonds.

A preferred type of functionalizing groups are imaging agents, which may be useful in a variety of applications, ex vivo and in vivo, in man as well as in an animal. The imaging agent can be selected from the group consisting of fluorescent dyes and metals, chromophoric dyes, phosphorescent compounds, chemiluminescent compounds and bioluminescent proteins, enzymes, radionuclides, radioactive particles and detectable nanoparticles, e.g. gold and semiconductor nanoparticles. A preferred imaging agent according to the invention is a fluorescent imaging agent, such as fluorescein. The imaging agent can be used for detection of the cross-linked HA. Applications can be to follow HA degradation in vivo and in vitro and to study the homogeneity of the cross-linking reaction. Cross-linked HA which is functionalized with an imaging agent can also be used to mark specific zones before surgery to assist the surgeon to locate the site of intervention with precision. Marking with cross-linked HA functionalized with an imaging agent can also be useful in radiotherapy treatments as a long-term but biodegradable way of marking zones to be irradiated or as pre-radiography location. Marking of a specific zone can be also of interest in clinical trials to accurately mark the place to be evaluated at each evaluation visit.

A preferred imaging agent according to the invention is a fluorescent imaging agent, such as fluorescein.

Unless otherwise provided, the terms "hyaluronic acid" and "HA" encompass all variants and combinations of variants of hyaluronic acid, or hyaluronan, of various chain lengths and charge states, as well as with various chemical modifications That is, the term also encompasses the various hyaluronate salts of hyaluronic acid, such as sodium hyaluronate. Various modifications of the hyaluronic acid are also encompassed by the term, such as oxidation, e.g. oxidation of $CH_2OH$ groups to COOH; periodate oxidation of vicinal hydroxyl groups, optionally followed by reduction or imine formation etc; reduction, e.g. reduction of COOH to $CH_2OH$; sulphation; deamidation, optionally followed by deamination or amide formation with new acids; esterification; substitutions with various compounds, e.g. using a cross-linking agent or a carbodiimide; including coupling of different molecules, such as proteins, peptides and active drug components, to hyaluronic acid; and deacetylation.

It is preferred that the hyaluronic acid substrate is a hyaluronic acid or hyaluronate salt without chemical modifications, i.e. which has not been subjected to cross-linking or other modifications prior to the present manufacturing method.

The hyaluronic acid can be obtained from various sources of animal and non-animal origin. Sources of non-animal origin include yeast and preferably bacteria. The molecular weight of a single hyaluronic acid molecule is typically in the range of 1.5-3 MDa, but other ranges of molecular weights are possible, e.g. 0.5-10 MDa.

Since the HA cross-linking step according to the invention involves traditional HA cross-linking chemistry, the skilled person is well aware of numerous ways and conditions to implement this step. By way of example, the cross-linking step may be performed as set out in U.S. Pat. No. 5,827,937. In brief, an aqueous solution of the HA is formed. Cross-linking of the HA is initiated in the presence of a mixture of (i) a first polyfunctional cross-linking agent selected from the group consisting of bifunctional epoxides and polyfunctional epoxides and (ii) a functionalized agent, consisting of a functionalizing group coupled via a 1,2,3-triazole linkage to a second cross-linking agent selected from the group consisting of bifunctional epoxides and polyfunctional epoxides. This cross-linking reaction may be allowed to continue up to the formation of a viscoelastic gel. Optionally, the cross-linking reaction is sterically hindered from terminating before gelation occurs, whereby an activated HA is obtained. Sterically unhindered conditions for the activated HA are reintroduced so as to continue the cross-linking thereof up to a viscoelastic gel.

In certain embodiments, any unreacted cross-linking agent and unreacted functionalized agent can be removed from the cross-linked HA containing the functionalizing group, e.g. by dialysis or filtration.

The present invention provides according to a second aspect a cross-linked hyaluronic acid containing a functionalizing group. The functionalizing group is coupled to the hyaluronic acid via a 1,2,3-triazole linkage and an ether linkage, and the hyaluronic acid is cross-linked using the same type of ether linkage.

An example of the product according to the invention is illustrated in FIG. 1, wherein the functionalizing group is termed "A". It is evident that the HA/HA cross-links involve ether bonds resulting from the cross-linking reaction of the HA with the cross-linking agent BDDE. In contrast, the cross-links between HA and the functionalizing group contain both (i) an ether bond resulting from the reaction of the HA with the cross-linking agent BDDE and (ii) a 1,2,3-triazole linkage between the BDDE residue and the functionalizing group.

As disclosed hereinabove, the functionalizing group may be any chemical molecule that it is desirable to incorporate by covalent bonds, or graft, into a cross-linked HA gel to provide a new function to the material. The skilled person is familiar with various types of functionalizing groups, which may have a biological, medicinal or technical activity or relevance.

It is preferred that the cross-linked HA containing a functionalizing group according to the invention is obtainable by the process set out hereinabove.

The product of the HA cross-linking reaction according to the invention is a gel, or a hydrogel. That is, it can be regarded as a water-insoluble, but substantially dilute cross-linked system of hyaluronic acid molecules when subjected to a liquid, typically an aqueous liquid. The gel is mostly liquid by weight and can e.g. contain 90-99.9% water, but it behaves like a solid due to a three-dimensional cross-linked hyaluronic acid network within the liquid. Due to its significant liquid content, the gel is structurally flexible and similar to natural tissue, which makes it very useful as a scaffold in tissue engineering and for tissue augmentation. It is the cross-links and their attachment positions at the hyaluronic acid molecules that, together with the natural entanglement of the hyaluronic acid chains, give the gel its structure and properties, which are intimately related to its swelling degree. Another characteristic of a gel is its capacity to absorb water until it is fully swollen. Further addition of liquid will not dilute the gel further, i.e. the gel cannot be indefinitely diluted like a solution of free molecules.

Furthermore, it is preferable that the cross-linked HA gel products according to the invention are viscoelastic. This implies that the gel products exhibit a combination of viscous and elastic properties. As is well known by the skilled person, the viscoelastic properties can be determined with a rheometer. In oscillating mode, the elastic modulus (G') and the viscous modulus (G") can be determined at a frequency of 0.1 or 1Hz. For certain viscoelastic gel products according to the invention, it is preferred that the following relationship is satisfied:

$$0.1 \leq \frac{G'}{(G'' + G')} \leq 0.98, \text{ preferably } 0.5 \leq \frac{G'}{(G'' + G')} \leq 0.98.$$

The cross-linked HA gel can be transformed into gel particles in any suitable way. One suitable way of obtaining a desired particle size involves producing a gel made of cross-linked hyaluronic acid at a desired concentration and subjecting the gel to physical disruption, such as mincing, mashing or allowing the gel to pass through a filter with suitable particle size. The resulting gel particles are dispersed in a physiological salt solution, resulting in a gel dispersion or slurry with particles of desired size, thus forming an implant.

An implant according to the invention may be an aqueous composition comprising the cross-linked HA product according to the invention, e.g. in the shape of ≥0.1 mm large HA gel particles, and optionally a buffering agent. The composition may typically contain a physiological salt buffer. The composition may further comprise other suitable additives, such as local anaesthetics (e.g. lidocaine hydrochloride), anti-inflammatory drugs, antibiotics and other suitable supportive medications, e.g. bone growth factors or cells. The cross-linked HA product according to the invention, or an aqueous composition thereof, may be provided in a pre-filled syringe, i.e. a syringe that is pre-filled with a sterilized, cross-linked HA product or a sterilized aqueous composition comprising the product.

According to the invention, the HA implant is administered, preferably injected, to the treated site in any suitable way. The implant, consisting of HA particles of a viscoelastic medium and optionally other suitable ingredients, may be administered as a single aliquot or as layers of multiple aliquots. Optionally, the implant may be replaced, refilled or replenished by a subsequent injection of HA particles of the same type. The injected volume is determined by the desired purpose. In a typical tissue augmentation, a volume in the range of 1-500 ml is injected, depending on the purpose and the treated tissue.

The cross-linked HA product according to the invention is useful in cosmetic or medical surgery. Non-limiting examples of cosmetic surgery are dermal filling and body contouring. Non-limiting examples of medical surgery are dermal filling, body contouring, prevention of tissue adhesion, orthopaedic applications, incontinence treatment, treatment of vesicoureteral reflux (VUR), and formation of channels for draining purposes, e.g. in ophthalmology, and for keeping tissues apart. The cross-linked HA product according to the invention is also useful in drug delivery. It can furthermore be used as a film for post-surgical (inter-peritorial) adhesion and in hip and joint therapy.

According to one aspect, the present invention provides a method of treatment of a subject undergoing cosmetic or medical surgery, involving administration of a cross-linked HA product according to the invention to a subject in need thereof. Non-limiting examples of medical surgery are dermal filling, body contouring, prevention of tissue adhesion, orthopaedic applications, e.g. hip and joint therapy, and formation of channels for draining purposes, e.g. in ophthalmology, and for keeping tissues apart The present invention provides according to a third aspect a functionalized agent. The functionalized agent consists of a functionalizing group coupled via a 1,2,3-triazole linkage to a cross-linking agent selected from bifunctional epoxides and polyfunctional epoxides.

As disclosed hereinabove, the functionalizing group may be any chemical molecule that it is desirable to incorporate by covalent bonds into a cross-linked HA gel to provide a new function to the material. The skilled person is familiar with various types of functionalizing groups, which may have a biological, medicinal or technical activity or relevance.

As set out for the bifunctional epoxide BDDE in FIG. 1, one of the epoxide groups is activated to produce a cross-linking agent carrying an azido group. It follows that one of the epoxide functions is modified with an azido function. The functional group of interest, termed A in FIG. 1, is activated by reaction of a suitable reactive group on the functionalizing group of interest to produce a functionalizing group carrying an alkyne group. The azide (epoxide cross-linking agent) and the alkyne (functionalizing group) are allowed to react and form a 1,2,3-triazole linking the cross-linking agent to the functionalizing group A, as shown for BDDE in FIG. 1. This reaction typically occurs in the presence of a catalyst, such as Cu. The resulting compound, a functionalized agent, can then be allowed to react with HA. This allows for use of the functionalized agent according to the invention for the manufacture of a cross-linked hyaluronic acid containing a functionalizing group as set out hereinabove. This also allows for use of the functionalized agent according to the invention and a cross-linking agent selected from the group consisting of bifunctional epoxides and polyfunctional epoxides for the simultaneous functionalizing and cross-linking of hyaluronic acid.

Without being limited thereto, the present invention will in the following be further illustrated by way of examples.

EXAMPLES

Example 1

Preparation of flurorescein-BDDE (fluo-BDDE)

A. 1-Azido-3-(4-oxiranylmethoxy-butoxy)-propan-2-ol

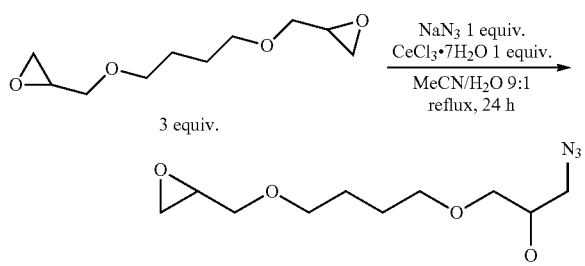

To a stirred solution of 1,4-butanediol diglycidyl ether (BDDE) (25.45 mL; 138.44 mmol; 3.00 eq.) and cerium(III) chloride heptahydrate (17.19 g; 46.15 mmol; 1.00 eq.) in acetonitrile (420.00 mL) and water (45.00 mL) (9:1 mixture) at r.t. was added sodium azide (3.00 g; 46.15 mmol; 1.00 eq.). The reaction mixture was stirred at 85° C. for 12 h and then cooled to r.t., diluted with EtOAc (300 mL) and water (500 mL). Phases were separated and the aqueous layer extracted with EtOAc (3×300 mL). The combined organic layers were washed with brine, dried (Na$_2$SO$_4$) and evaporated to dryness to yield a pale yellow oil. This oil was purified by flash chromatography (SiO$_2$, DCM/MTBE 9:1) to furnish the desired product (R$_f$=0.27) as a colorless oil (m=8.01 g, 70%).

$^1$H NMR (400 MHz, CDCl$_3$) δ (ppm): 1.65-1.67 (m, 4H), 2.61 (dd, J=5.03; 2.71 Hz, 1H), 2.80 (dd, J=5.01; 4.16 Hz, 1H), 3.15 (dt, J=6.23; 3.31 Hz, 1H), 3.32-3.41 (m, 2H), 3.43-3.67 (m, 7H), 3.69-3.79 (m, 1H), 3.89-4.02 (m, 1H).

$^{13}$C NMR (50 MHz, CDCl3) δ (ppm): 26.1, 26.2, 44.1, 46.1, 50.8, 69.5, 70.1, 71.1, 71.3, 71.9.

B. Acetylene-fluorescein

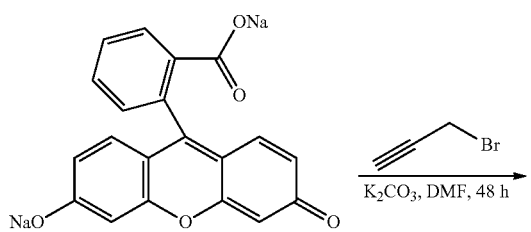

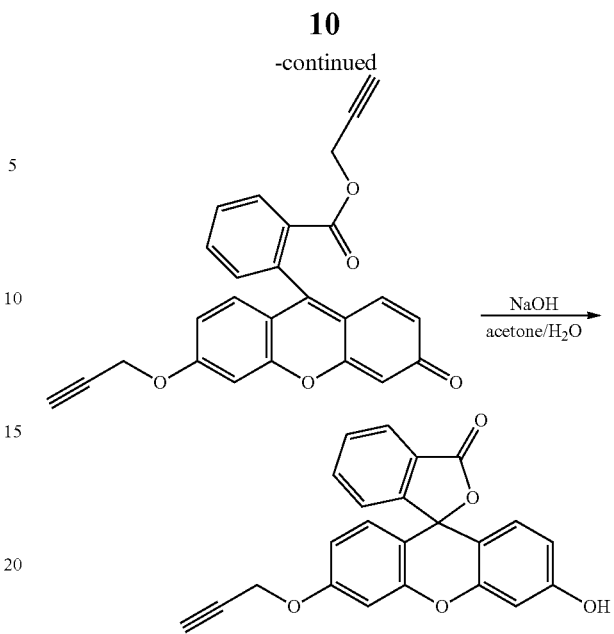

To a stirred solution of fluorescein sodium salt (15.00 g; 45.14 mmol; 1.00 eq.) and potassium carbonate (18.71 g; 0.14 mol; 3.00 eq.) in N,N-dimethylformamide (30.00 mL) at r.t. was added propargyl bromide (50.28 mL of a 80% w/w solution in toluene; 451.38 mmol; 10.00 eq.). The reaction mixture was stirred at r.t. for 96 hours. LCMS analysis of the crude reaction mixture after this time showed almost mainly the desired product (m/z=408). The reaction mixture was filtered and evaporated to dryness. To the orange solid obtained was added acetone (150.00 mL) followed by a solution of sodium hydroxide (21.66 g; 541.66 mmol; 12.00 eq.) in water (75.00 mL). The suspension (which slowly turned to a solution) was stirred at r.t. for 18 h. The reaction mixture was acidified to pH=3, by the careful addition of 2N aqueous HCl and acetone was evaporated under vacuum. The aqueous phase was extracted with DCM (3×150 mL) and the combined organic layers washed with brine, dried (MgSO4) and evaporated to dryness to yield a dark brown oil. This oil was purified by flash column chromatography (SiO$_2$, DCM/MeOH 98:2 to 95:5) to furnish the desired product as a yellow solid (m=3.2 g, 19%).

$^1$H NMR (400 MHz, CDCl3) δ (ppm): 2.56 (t, J=2.4 Hz, 1H), 4.71 (d, J=2.4 Hz, 2H), 6.52 (dt, J=2.2; 8.7 Hz, 1H), 6.57 (d, J=8.7 Hz, 1H), 6.66 (dt, J=2.2; 8.8 Hz, 1H), 6.70 (d, J=8.8 Hz, 1H), 6.74 (d, J=2.2 Hz, 1H), 6.85 (d, J=2.2 Hz, 1H), 7.16 (d, J=7.6 Hz, 1H), 7.62 (dd, J=7.6; 8.0 Hz, 1H), 7.67 (dd, J=7.4; 8.0 Hz, 1H), 8.02 (d, J=7.4 Hz, 1H).

$^{13}$C NMR (50 MHz, CDCl3) δ (ppm): 56.0, 76.2, 77.8, 84.4, 102.1, 103.2, 110.7, 111.9, 112.1, 112.5, 124.0, 125.1, 126.6, 129.1, 129.2, 129.8, 135.2, 152.4, 153.0, 158.2, 159.2, 170.2.

C. Fluorescein-BDDE (Fluo-BDDE)

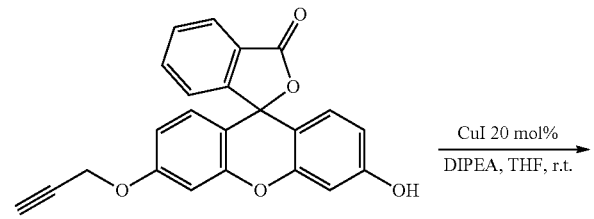

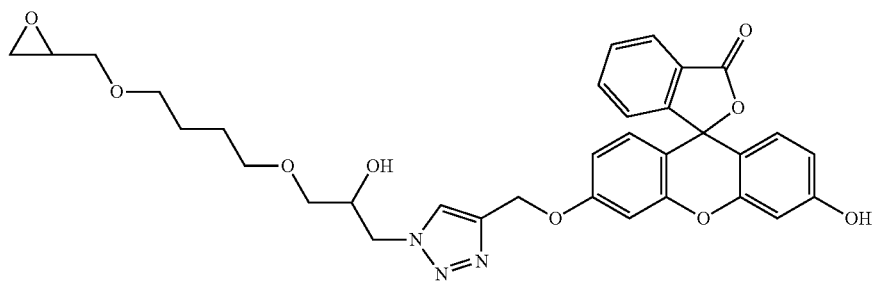

To a stirred solution of acetylene-fluorescein (3.00 g; 8.10 mmol; 1.00 eq.) and 1-azido-3-(4-oxiranylmethoxy-butoxy)-propan-2-ol (2.98 g; 12.15 mmol; 1.50 eq.) in tetrahydrofuran (45.00 mL) at r.t. was added N,N-diisopropylethylamine (4.18 mL; 24.30 mmol; 3.00 eq.) and finally copper (I) iodide (0.15 g; 0.81 mmol; 0.10 eq.). The reaction mixture was stirred at r.t. for 6 h. After that time, LCMS analysis showed only 70% conversion. More 1-azido-3-(4-oxiranylmethoxy-butoxy)-propan-2-ol (1.00 g; 4.05 mmol; 0.50 eq.) and copper (I) iodide (0.15 g; 0.81 mmol; 0.10 eq.) were added and the reaction mixture was stirred at r.t. for 18 h. LCMS analysis showed a complete conversion after that time. The reaction mixture was diluted with saturated aqueous NH$_4$Cl (150 mL) and 1N aqueous HCl (50 mL) and extracted with ethyl acetate (3×100 mL). The combined organic layers were washed with brine (100 mL), dried (Na$_2$SO$_4$) and evaporated to dryness. The orange oil obtained was purified by flash column chromatography (SiO$_2$, DCM/MeOH 95:5) to yield a mixture of the product 1-azido-3-(4-oxiranylmethoxy-butoxy)-propan-2-ol. This oil was dissolved in DCM (20 mL) and the product precipitated by the slow addition of MTBE (100 mL). The product was collected by filtration as an orange solid (1.90 g; 38%) which was used as such for hyaluronic acid cross-linkage.

$^1$H NMR (400 MHz, CDCl3) δ (ppm): 1.59-1.67 (m, 4H), 2.59-2.60 (m, 1H), 2.79 (t, J=4.5 Hz, 1H), 3.12-3.18 (m, 1H), 3.26-3.39 (m, 3H), 3.42-3.56 (m, 6H), 3.75 (dd, J=11.6; 2.7 Hz, 1H), 4.13-4.20 (m, 1H), 4.35-4.44 (m, 1H), 4.49-4.58 (m, 1H), 5.19 (br s, 2H), 6.53 (dd, J=8.7; 2.4 Hz, 1H), 6.58-6.73 (m, 4H), 6.84 (t, J=2.7 Hz, 1H), 7.13 (d, J=7.5 Hz, 1H), 7.55-7.67 (m, 2H), 7.78 (s, 1H), 8.00 (d, J=7.5 Hz, 1H).

$^{13}$C NMR (50 MHz, CDCl3) δ (ppm): 26.2, 26.3, 44.3, 51.0, 53.2, 61.8, 69.1, 71.2, 71.3, 71.5, 71.6, 102.0, 103.2, 110.7, 112.0, 113.5, 113.8, 124.4, 124.8, 125.3, 127.4, 129.2, 129.3, 129.7, 134.8, 143.0, 151.6, 151.8, 152.6, 152.8, 160.0, 160.1, 170.0.

Conclusion: The click CuAAC reaction between azido-epoxide and alkyne-fluorescein works well under organic and aqueous conditions.

Example 2

Functionalization of Cross-Linked HA with Fluorescein

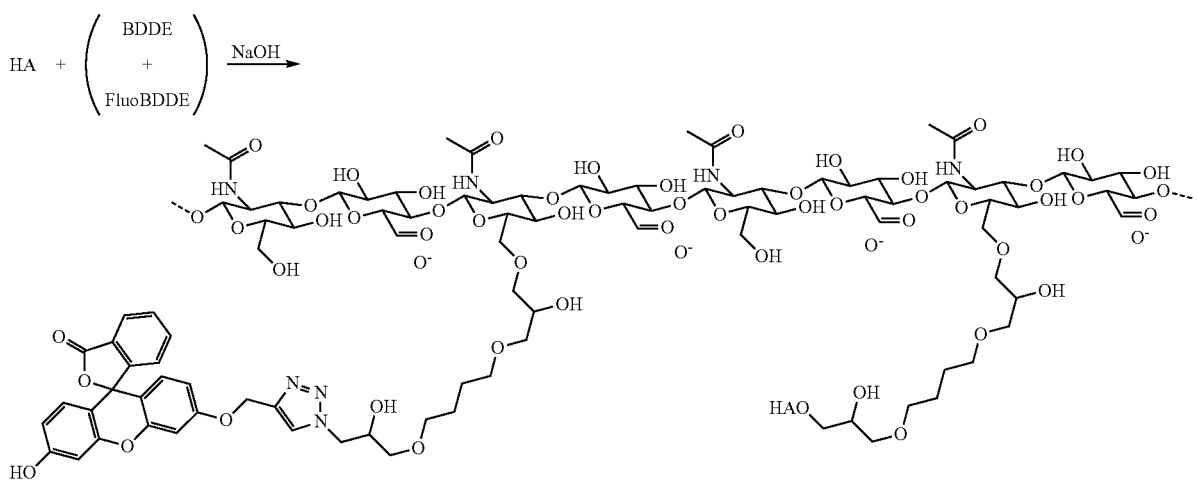

As previously exemplified in e.g. U.S. Pat. No. 5,827,937, 10 g of hyaluronic acid prepared by fermentation of Streptococcus is dissolved in 100 ml of 1% NaOH, pH>9. Cross-linking agent in the form of a mixture of BDDE and Fluo-BDDE in ratios of from 1:10 to 10:1 is added to a total concentration of 0.2%. The solution is incubated at 40° C. for 4 h.

The incubated solution is diluted with an acidic water solution to reach neutral pH under mixing, yielding a final hyaluronic acid concentration of 20 mg/ml, and again incubated for 12 h at 70° C. The viscoelastic gel that resulted from this second incubation is then cooled to room temperature and mashed to its final particle size, approximately 0.5-1 mm. The gel particles are washed and sterilized by heat or radiation.

The invention claimed is:

1. A process for manufacturing a cross-linked hyaluronic acid (HA) containing a functionalizing group, comprising a step of reacting HA in a single step with a mixture of:
   (i) a first cross-linking agent selected from a group consisting of bifunctional epoxides and polyfunctional epoxides, and
   (ii) a functionalized agent, consisting of a functionalizing group coupled via a 1,2,3-triazole linkage to a second cross-linking agent selected from the group consisting of bifunctional epoxides and polyfunctional epoxides, to obtain a cross-linked HA containing the functionalizing group.

2. A process according to claim 1, wherein the first and second cross-linking agents are independently selected from the group consisting of bifunctional epoxides and polyfunctional epoxides, and wherein the reacting step is performed at a basic pH to provide ether cross-links both between the HA and the first cross-linking agent, and between the HA and the functionalized agent.

3. A process according to claim 2, wherein the first and second cross-linking agents are independently selected from the group consisting of bifunctional epoxides.

4. A process according to claim 3, wherein the first and second cross-linking agents are both butanediol diglycidyl ether (BDDE).

5. A process according to claim 1, wherein the functionalizing group is an imaging agent.

6. A process according to claim 5, wherein the imaging agent is fluorescein.

* * * * *